United States Patent
Shepard

(10) Patent No.: US 7,407,668 B2
(45) Date of Patent: Aug. 5, 2008

(54) MEDICAL ARTICLES HAVING ENZYMATIC SURFACES FOR LOCALIZED THERAPY

(75) Inventor: Douglas C. Shepard, Mansfield, MA (US)

(73) Assignee: Boston Scimed, Inc., Maple Grove, MN (US)

( * ) Notice: Subject to any disclaimer, the term of this patent is extended or adjusted under 35 U.S.C. 154(b) by 1256 days.

(21) Appl. No.: 10/057,596

(22) Filed: Jan. 24, 2002

(65) Prior Publication Data

US 2003/0138415 A1 Jul. 24, 2003

(51) Int. Cl.
- *A61F 13/00* (2006.01)
- *A61L 15/16* (2006.01)
- *A61M 5/00* (2006.01)
- *A61K 9/22* (2006.01)

(52) U.S. Cl. .............. 424/422; 424/423; 424/426; 424/484; 424/447; 530/402; 604/264; 604/890.1; 604/891.1

(58) Field of Classification Search ......... 424/422–433, 424/484–488; 530/402; 604/264, 890.1, 604/891.1

See application file for complete search history.

(56) References Cited

U.S. PATENT DOCUMENTS

| | | | |
|---|---|---|---|
| 4,378,435 A | 3/1983 | Takagi et al. | |
| 4,525,456 A | 6/1985 | Rohrbach | 435/176 |
| 4,613,502 A * | 9/1986 | Turkova et al. | 424/94.3 |
| 4,855,234 A * | 8/1989 | Hendrickson et al. | 435/181 |
| 5,741,331 A * | 4/1998 | Pinchuk | 424/423 |
| 5,759,836 A * | 6/1998 | Amin et al. | 435/189 |
| 5,788,678 A * | 8/1998 | Van Antwerp | 604/265 |
| 5,840,190 A * | 11/1998 | Scholander et al. | 210/500.24 |
| 6,024,918 A | 2/2000 | Hendriks et al. | 422/44 |
| 6,033,719 A | 3/2000 | Keogh | 422/2.12 |
| 6,077,714 A | 6/2000 | Spallholz et al. | 436/525 |
| 6,177,282 B1 * | 1/2001 | McIntyre | 436/518 |
| 6,569,688 B2 * | 5/2003 | Sivan et al. | 436/518 |

OTHER PUBLICATIONS

Senatore et al., "Fibrinolytic activity of immobilized plasminogen activator," Res Commun Chem Pathol Pharmacol Aug. 1985:49(2) 295-304, Abstract only.

Forster et al., "Analysis of urokinase immobilization on the polytetrafluoroethylene vascular prosthesis," Am J Surg 1988: 156(2): 130-2, Abstract only.

Harvey et al., "Binding of tissue plasminogen activator to vascular grafts," Thromb Haemost Feb. 1989;61(1):131-6, Abstract Only.

Jefferies et al., "Preliminary studies with L-asparaginases bound to implantable bovine collagen heterografts: a potential long-term, sustained dosage, antitumor enzyme therapy system," Biomater Med Devices Artif Organs 1977;5(4):3337-54, Abstract Only.

Raghavan et al., "Degradation of oxalate in rats implanted with immobilized oxalate oxidase," FEBS Lett Jan. 20, 1986;195(1-2):101-5, Abstract Only.

Jamie Y. Jeremy et al., "Nitric oxide and the proliferation of vascular smooth muscle cells," Cardiovascular Research Aug. 15, 1999;43(3):580-94.

* cited by examiner

*Primary Examiner*—Gollamudi Kishore
(74) *Attorney, Agent, or Firm*—Mayer & Williams PC; David B. Bonham, Esq.; Keum J. Park, Esq.

(57) ABSTRACT

An enzymatically active medical article is provided, which comprises a medical article and an enzyme disposed at or near a surface of the medical article such that the medical article is provided with an enzymatically active surface. The enzyme is selected, for example, from the group consisting of protease enzymes, glycosidase enzymes, enzymes that degrade cholesterol esters, enzymes that convert hydrocortisone to cortisone, enzymes that degrade oxalate, and enzymes that generate NO from arginine.

32 Claims, No Drawings

MEDICAL ARTICLES HAVING ENZYMATIC SURFACES FOR LOCALIZED THERAPY

FIELD OF THE INVENTION

The present invention relates to compositions and techniques for localized therapy. More particularly, the present invention is relates to medical articles for localized therapy that have enzymatically active surfaces and to methods of therapy using the same.

BACKGROUND OF THE INVENTION

At present, numerous therapeutic techniques involve the systemic delivery of one or more therapeutic agents or the systemic removal of an undesirable chemical entity. Systemic delivery and removal techniques, however, are not well suited to all therapies.

For instance, systemic delivery requires exposing sites other than the site of interest to a therapeutic agent. Indeed, large quantities of therapeutic agent within the entire system are often required to obtain the desired effect at a desired site. As a result, the therapeutic agent concentration at the site of interest is often limited by the detrimental effects of the agent at sites remote from the site of interest.

Systemic delivery techniques are also commonly undesirable in that the therapeutic agent is degraded and eliminated by an organ system(s) remote from the site of interest.

Systemic removal techniques are also frequently undesirable, because a chemical entity that is undesirable at one specific site may be useful, or even essential, at another site.

The above problems can be avoided by techniques in which a therapeutic agent is locally provided at a site of interest or an undesirable chemical entity is locally removed from a site of interest.

In response to this recognition, techniques and articles for the localized delivery of therapeutic agents to bodily tissue, and for the localized removal of undesirable chemical entities from bodily tissue, have been developed.

SUMMARY OF THE INVENTION

The present invention provides novel compositions and techniques for localized supply or removal of various therapeutic agents to the body.

According to an embodiment of the invention, an enzymatically active medical article is provided, which comprises a medical article and an enzyme disposed at or near a surface of the medical article such that the medical article is provided with an enzymatically active surface. The enzyme is preferably selected from the group consisting of protease enzymes, glycosidase enzymes, enzymes that degrade cholesterol esters, enzymes that convert hydrocortisone to cortisone, enzymes that degrade oxalate and enzymes that generate NO from arginine.

In some embodiments, the enzyme is provided within a biocompatible, biostable matrix coating disposed on the medical article. In others, the enzyme is attached to a surface of the medical article. For example, the enzyme can be: (a) covalently attached to a surface of the medical article, (b) attached to the surface of the medical article by ion exchange forces, (c) attached to the surface of the medical article by antibody-antigen interactions, and/or (d) attached to the surface of the medical article by nucleic-acid hybridization. In some instances, the device further comprises an enzyme-free coating layer, which acts to protect the enzyme from the immune system of the patient.

The medical article can be, for example, a catheter, a guide wire, a balloon, a filter, a stent, a stent graft, a cerebral aneurysm filler, a vascular graft, a heart valve, a bandage or a bulking agent. In several preferred embodiments, the medical article is a vascular medical device.

In other embodiments, the above enzymatically active medical article is administered to a patient, preferably vertebrate patient, more preferably a mammalian patient, and most preferably a human patient.

Specific embodiments include the following: (a) the enzyme is an enzyme that converts hydrocortisone to cortisone, and the medical article is administered to a site of inflammation, (2) the enzyme is an enzyme that generates NO from arginine, and the medical article is administered to a site within the vasculature to prevent restenosis, (3) the enzyme is an enzyme that acts upon cholesterol esters, and the medical article is placed adjacent atherosclerotic plaque within the vasculature to degrade the cholesterol ester deposits found in the atherosclerotic plaque, (4) the enzyme is a glycosidase enzyme effective to degrade ceramide trihexoside in the treatment of Fabray's disease, and the medical article is a blood contacting device, (5) the enzyme is a glycosidase enzyme effective to degrade glucocerebroside in the treatment of Gaucher's disease, and the medical article is a blood contacting device, (6) the enzyme is a glycosidase enzyme effective to degrade ganglioside GM2 in the treatment of Tay-Sach's disease, and the medical article is implanted within the cranium.

One advantage of the present invention is that therapeutic agents can be locally supplied to, and undesirable chemical entities can be removed from, a site of interest.

Another advantage is that therapeutic agents can be provided at a site of interest without a significant increase in concentration of therapeutic agent at sites remote from the delivery site.

Another advantage of this aspect of the present invention is that a self-cleaning medical article is provided.

Yet another advantage is that a non-therapeutically effective or marginally therapeutically effective substrate molecule can be converted to a highly therapeutically effective molecule at a local site.

Another advantage is that harmful or potentially harmful substrates can be converted to a less harmful species at a local site.

These and other aspects, embodiments and advantages of the present invention will become immediately apparent to those of ordinary skill in the art upon reading the disclosure to follow.

DETAILED DESCRIPTION OF THE INVENTION

The present invention is directed to novel articles and techniques for localized therapy. According to an embodiment of the invention, a medical article is provided with an enzymatic surface, thereby providing the surface of the article with catalytic activity.

Medical articles appropriate for the practice of the invention include essentially any medical article that can be exposed to bodily tissue and fluids. These articles include both vascular and non-vascular medical articles. Preferred non-vascular articles include bulking agents, bandages and wraps. Preferred vascular articles include vascular catheters (for example, coated balloon catheters, injection catheters or infusion catheters), coated or uncoated stents (including vascular stents and cerebral stents), stent grafts, vascular grafts, shunts, aneurysm fillers (including Guglielmi detachable coils), intraluminal paving systems, guide wires, heart valves, balloons, embolic agents (for example polymeric particles, spheres, and liquid embolics) and filters (for example, vena cava filters).

Preferred sites for placement of the medical articles include the skin (for example, on skin wounds or over openings), coronary vasculature, peripheral vasculature, esophagus, trachea, colon, gastrointestinal tract, biliary tract, urinary tract, prostate, brain and surgical sites.

The medical article can be provided with a catalytic surface in a number of ways. For example, techniques for placing an enzyme at or near a surface of an article include (a) attachment of the enzyme to surface regions of the medical article, and (b) disposition of the enzyme within polymer matrices associated with the article.

Attachment techniques include covalent attachment techniques, as well as non-covalent attachment techniques, such as ion exchange techniques, antibody-antigen techniques and so forth.

Covalent attachment may be carried out in numerous ways. For example, the surface of the medical article can be treated with a reagent that places chemically reactive groups on the article surface. These groups are then reacted with groups commonly found on enzymes, such as amines, alcohols, carboxylic acids, and thiols.

In other cases, the medical article is provided with a coating that supplies a functional group of interest. Specific techniques can be found, for example, in (a) U.S. Pat. No. 6,033,719 entitled "Method for covalent attachment of biomolecules to surfaces of medical articles" in which a biomolecule comprising a 1,2 dicarbonyl moiety is combined with a material comprising a guanidine moiety to immobilize biomolecules, and (b) U.S. Pat. No. 6,024,918 entitled "Method for Attachment of Biomolecules to surfaces of medical articles" in which a substrate surface is coated with an amino-functional polysiloxane and subsequently exposed to a biomolecule.

An example of a non-covalent technique for holding an enzyme on a medical article surface is found in U.S. Pat. No. 4,525,456 entitled "Support Matrix and immobilized enzyme system", which describes a system in which a water-insoluble, functionalized polyethyleneimine, which is subsequently used to immobilize enzymes by ion exchange forces, is disposed on a support.

Other examples of non-covalent binding include protein-based techniques (e.g., antibody-antigen interactions) and nucleic-acid-hybridization based techniques (e.g., enzymatic RNA), both of which are known in the art. For example, it is known in the art to coat medical articles with heparin using protein-based processes of this type. Avidin-based technologies are another preferred group of attachment techniques.

In the instances where the enzyme is disposed within a polymer matrix associated with the article, the enzyme is preferably held within the matrix, rather than released from it. Hence, preferred matrices are biocompatible, biostable matrices that will hold the enzyme in place, while at the same time allowing diffusion of substrates into and diffusion of products out of the matrix. By "biostable" is meant a polymer that does not substantially degrade in vivo. Thus, a biostable polymer is one that maintains its structural integrity, i.e., is substantially inert, in the presence of a physiological environment.

The matrix or matrices can constitute the entire medical article or a distinct portion of a medical article (for example, a discrete article component, a portions of an article component, a coating on the article surface, and so forth).

Preferred biocompatible, biostable polymers include numerous thermoplastic and elastomeric polymeric materials that are known in the art. Polyolefins such as metallocene catalyzed polyethylenes, polypropylenes, and polybutylenes and copolymers thereof; ethylenic polymers such as polystyrene; ethylenic copolymers such as ethylene vinyl acetate (EVA), ethylene-methacrylic acid and ethylene-acrylic acid copolymers where some of the acid groups have been neutralized with either zinc or sodium ions (commonly known as ionomers); polyacetals; chloropolymers such as polyvinylchloride (PVC); fluoropolymers such as polytetrafluoroethylene (PTFE); polyesters such as polyethylene terephthalate (PET); polyester-ethers; polysulfones; polyamides such as nylon 6 and nylon 6,6; polyamide ethers; polyethers; elastomers such as elastomeric polyurethanes and polyurethane copolymers; silicones; polycarbonates; and mixtures and block or random copolymers of any of the foregoing are non-limiting examples of biostable biocompatible polymers useful for manufacturing the medical devices of the present invention.

Additional preferred biocompatible biostable polymers, which are not necessarily exclusive of those listed in the prior paragraph, are described in U.S. Pat. No. 6,153,252, the disclosure of which is incorporated by reference. These polymers include polyurethanes, silicones, poly(meth)acrylates, polyesters, polyalkylene oxides such as polyethylene oxide, polyvinyl alcohols, polyethylene glycols and polyvinyl pyrrolidone; hydrogels such as those formed from crosslinked polyvinyl pyrrolidinone and polyesters could also be used. Other polymers include polyolefins, polyisobutylene and ethylene-alphaolefin copolymers; acrylic polymers (including methacrylic polymers) and copolymers, vinyl halide polymers and copolymers, such as polyvinyl chloride; polyvinyl ethers, such as polyvinyl methyl ether; polyvinylidene halides such as polyvinylidene fluoride and polyvinylidene chloride; polyacrylonitrile, polyvinyl ketones; polyvinyl aromatics such as polystyrene; polyvinyl esters such as polyvinyl acetate; copolymers of vinyl monomers with each other and olefins, such as ethylene-methyl methacrylate copolymers, acrylonitrile-styrene copolymers, ABS resins and ethylene-vinyl acetate copolymers; polyamides, such as nylon 6,6 and polycaprolactam; alkyd resins; polycarbonates; polyoxymethylenes; polyimides; polyethers; epoxy resins, polyurethanes; rayon; rayon-triacetate, cellulose, cellulose acetate, cellulose acetate butyrate; cellophane; cellulose nitrate; cellulose propionate; cellulose ethers (i.e. carboxymethyl cellulose and hydroxyalkyl celluloses); and combinations thereof. Polyamides for the purpose of this application would also include polyamides of the form —NH—$(CH_2)_n$—CO—and NH—$(CH_2)_x$—NH—CO—$(CH_2)_y$—CO, wherein n is preferably an integer in from 6 to 13; x is an integer in the range of form 6 to 12; and y is an integer in the range of from 4 to 16. Mixtures and block or random copolymers of any of the foregoing are also useful in the present invention.

Among the more preferred biostable polymeric materials are polyolefins, polyolefin-polyvinylaromatic copolymers including polystyrene-polyisobutylene copolymers and butadiene-styrene copolymers, ethylenic copolymers including ethylene vinyl acetate copolymers (EVA) and copolymers of ethylene with acrylic acid or methacrylic acid; elastomeric polyurethanes and polyurethane copolymers; metallocene catalyzed polyethylene (mPE), mPE copolymers; ionomers; polyester-ethers; polyamide-ethers; silicones; and mixtures and copolymers thereof.

Also among the more preferred biostable polymeric materials are block copolymers having at least two polymeric blocks A and B. Examples of such block copolymers include the following: (a) BA (linear diblock), (b) BAB or ABA (linear triblock), (c) B(AB)$_n$ or A(BA)$_n$ (linear alternating block), or (d) X-(AB)$_n$ or X-(BA)$_n$ (includes diblock, triblock and other radial block copolymers), where n is a positive whole number and X is a starting seed molecule. One specific preferred group of polymers have X-(AB)$_n$ structures, which are frequently referred to as diblock copolymers and triblock copolymers where n=1 and n=2, respectively (this terminology disregards the presence of the starting seed molecule, for example, treating A-X-A as a single A block with the triblock therefore denoted as BAB). Where n=3 or more, these structures are commonly referred to as star-shaped block copolymers.

The A blocks are preferably soft elastomeric components which are based upon one or more polyolefins, more preferably a polyolefinic block having alternating quaternary and secondary carbons of the general formulation: —(CRR'—CH$_2$)$_n$—, where R and R' are linear or branched aliphatic groups such as substituted or unsubstituted methyl, ethyl, propyl, isopropyl, butyl, isobutyl and so forth, or substituted or unsubstituted cyclic aliphatic groups such as cyclohexane, cyclopentane, and the like. Polymers of isobutylene,

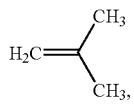

(i.e., polymers where R and R' are the same and are methyl groups) are more preferred.

The B blocks are preferably hard thermoplastic blocks that, when combined with the soft A blocks, are capable of, inter alia, altering or adjusting the hardness of the resulting copolymer to achieve a desired combination of qualities. Preferred B blocks are polymers of methacrylates or polymers of vinyl aromatics. More preferred B blocks are (a) made from monomers of styrene,

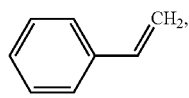

styrene derivatives (e.g., α-methylstyrene, ring-alkylated styrenes or ring-halogenated styrenes) or mixtures of the same or are (b) made from monomers of methylmethacrylate, ethylmethacrylate hydroxyethyl methacrylate or mixtures of the same.

Preferred seed molecules are those known in the art and include tert-ester, tert-ether, tert-hydroxyl or tert-halogen containing compounds, and more typically cumyl esters of hydrocarbon acids, alkyl cumyl ethers, cumyl halides and cumyl hydroxyl compounds as well as hindered versions of the above.

Particularly preferred polymers within this category include copolymers of polyisobutylene with polystyrene or polymethylstyrene, even more preferably polystyrene-polyisobutylene-polystyrene triblock copolymers. These polymers are described, for example, in U.S. Pat. No. 5,741,331, U.S. Pat. No. 4,946,899 and U.S. Ser. No. 09/734,639, each of which is hereby incorporated by reference in its entirety.

In certain applications, it will be advantageous to hide the surface enzyme from the body's immune surveillance. Under these circumstances, additional coatings, such as hydrogel coatings, can be applied over the enzyme.

Numerous embodiments of the present invention are contemplated. In some embodiments, enzymes held on the surface of the medical article can be used to provide a self-cleaning article. As a specific example, proteases attached to the surface of the article can be used to clean the surface of attached proteins.

In other embodiments, the enzyme will act upon a substrate found in a bodily fluid, such as blood, urine, tears, gastrointestinal fluids, saliva, bile or lymph, or in or on bodily tissue.

In some of these embodiments, a substrate molecule with marginal or no therapeutic efficacy is converted to a therapeutically effective molecule. For example, in some embodiments of the present invention, a prodrug within the bloodstream is converted into an active counterpart at a specific site of interest. As a specific example, hydrocortisone can be converted to cortisone using an esterase enzyme, ensuring that the treatment site, which is adjacent to or upstream of the enzyme, is exposed to elevated levels of the active compound.

As another example, one or more enzymes that generate NO from arginine for example, nitric oxide synthetase, are provided at or near the surface of a medical article. Such enzymes are preferably provided in connection with vascular medical devices, such as those listed above. When placed at a site of interest, such devices generate NO from arginine in the blood. NO is noted for its ability to prevent restenosis (e.g., by impeding proliferation of vascular smooth muscle in damaged vessels) and for its ability to relax vascular smooth muscle and improve perfusion in poorly oxygenated tissues, among others. The NO generated in this fashion is thus provided locally and downstream from the article, providing a beneficial function.

In others of these embodiments, a harmful or potentially harmful substrate will be converted to a less harmful species. For example, an enzyme that degrades oxalate (preventing calcium oxalate crystals and hence kidney stones from forming) can be provided on the surface of a catheter in the urinary tract. Such an enzyme is available from Sigma Chemical Co, Catalog number 04878. See also *FEBS Lett*. Jan. 20, 1986; 195(1-2); 101-5, in which dialysis membrane capsules containing immobilized oxalate oxidase were shown to intraperitoneally metabolize oxalate, as well as its glyoxalate precursor, in rats.

As another example, a glycosidase enzyme, such as α-galactosidase, β-galactosidase or β-glucosidase disposed on a filter or other blood contacting device can be placed such that it is exposed to blood flow (or, for example, at the site of the accumulation of lipid, such as the brain in the case of Tay-Sachs disease), allowing, for instance, a product associated with an inborn error of metabolism to be degraded. For example, ceramide trihexoside is degraded in connection with the treatment of Fabray's disease, glucocerebroside is degraded in connection with the treatment of Gaucher's disease, and ganglioside GM2 is degraded in connection with the treatment of Tay-Sach's disease.

As another example, an enzyme can be provided that acts upon a substrate found in solid tissue, including diseased tissue. For example, an enzyme can be disposed on or within a medical article that is introduced into the vasculature to degrade the cholesterol ester deposits found in atherosclerotic plaque. Exemplary enzymes include cholesterol esterase and cholesterol oxidase.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An enzymatically active medical article comprising:

a medical article having a matrix disposed on said article, wherein the matrix comprises a block copolymer comprising a polyolefinic block comprising polybutylene and a thermoplastic block comprising polymers of acrylates, methacrylates or vinyl aromatics, an enzyme disposed within said matrix and at or near a surface of said medical article, such that said medical article is provided with an enzymatically active surface, wherein said matrix allows diffusion of substrates into and diffusion of products out of the matrix, wherein said enzyme is elected from the group consisting of protease enzymes, glycosidase enzymes, enzymes that degrade oxalate, and enzymes that generate NO from arginine.

2. The enzymatically active medical article of claim 1, wherein said enzyme is a protease enzyme.

3. The enzymatically active medical article of claim 1, wherein said enzyme is an enzyme that degrades cholesterol esters.

4. The enzymatically active medical article of claim 3, wherein said enzyme is selected from cholesterol esterase and cholesterol oxidase.

5. The enzymatically active medical article of claim 1, wherein said enzyme is an enzyme that converts hydrocortisone to cortisone.

6. The enzymatically active medical article of claim 5, wherein said enzyme is a hydrocortisone esterase enzyme.

7. The enzymatically active medical article of claim 1, wherein said enzyme is a glycosidase enzyme.

8. The enzymatically active medical article of claim 7, wherein said enzyme is an α-galactosidase enzyme.

9. The enzymatically active medical article of claim 7, wherein said enzyme is a β-galactosidase enzyme.

10. The enzymatically active medical article of claim 7, wherein said enzyme is a β-glucosidase enzyme.

11. The enzymatically active medical article of claim 1, wherein said enzyme is an enzyme that generates NO from arginine.

12. The enzymatically active medical article of claim 11, wherein said enzyme is nitric oxide synthetase.

13. The enzymatically active medical article of claim 11, wherein said enzyme is provided within a biocompatible, biostable matrix coating disposed on said medical article.

14. The enzymatically active medical article of claim 11, wherein said enzyme is attached to a surface of said medical article.

15. The enzymatically active medical article of claim 14, wherein said enzyme is covalently attached to a surface of said medical article.

16. The enzymatically active medical article of claim 14, wherein said enzyme is attached to a surface of said medical article by ion exchange forces.

17. The enzymatically active medical article of claim 14, wherein said enzyme is attached to a surface of said medical article by antibody-antigen interactions.

18. The eazyinatically active medical article of claim 14, wherein said enzyme is attached to a surface of said medical article by nucleic-acid hybridization.

19. The enzymatically active medical article of claim 14, wherein said enzyme is attached to a surface coating on said medical device.

20. The enzymatically active medical article of claim 1, further comprising an enzyme-free coating layer provided over said enzyme, wherein said enzyme-free coating layer acts to hide said enzyme from immune surveillance.

21. The enzymatically active medical article of claim 1, wherein said medical article is a vascular medical device.

22. The enzymatically active medical article of claim 1, wherein said medical article is selected from a catheter, a guide wire, a balloon, a filter, a stent, a stent graft, a cerebral aneurysm filler, a vascular graft, a heart valve, a bandage and a bulking agent.

23. A therapeutic method comprising:
providing the enzymatically active medical article of claim 1; and
administering said medical article to a patient.

24. The therapeutic method of claim 23, wherein said medical article is a vascular medical device.

25. The therapeutic method of claim 23, wherein said enzyme is an enzyme that converts hydrocortisone to cortisone and wherein said medical article is administered to a site of inflammation.

26. The therapeutic method of claim 23, wherein said enzyme is an enzyme that converts hydrocortisone to cortisone and wherein said medical article is administered to a site of inflammation.

27. The therapeutic method of claim 23, wherein said enzyme is an enzyme that generates NO from arginine and wherein said medical article is administered to a site within the vasculature to prevent restenosis.

28. The therapeutic method of claim 23, wherein said enzyme is an enzyme that acts upon cholesterol esters and wherein said medical article is placed adjacent atherosclerotic plaque within the vasculature to degrade the cholesterol ester deposits found in said atherosclerotic plaque.

29. The therapeutic method of claim 23, wherein said enzyme is a glycosidase enzyme effective to degrade ceramide trihexoside in the treatment of Fabray's disease and wherein said medical article is a blood contacting device.

30. The therapeutic method of claim 23, wherein said enzyme is a glycosidase enzyme effective to degrade glycocerebroside in the treatment of Gaucher's disease and wherein said medical article is a blood contacting device.

31. The therapeutic method of claim 23, wherein said enzyme is a glycosidase enzyme effective to degrade ganglioside GM2 in the treatment of Tay-Sach's disease and wherein said medical article is implanted within the cranium.

32. The therapeutic method of claim 23, wherein said enzyme is oxalte oxidase and wherein said medical article is a urinary catheter.

* * * * *

UNITED STATES PATENT AND TRADEMARK OFFICE
CERTIFICATE OF CORRECTION

PATENT NO. : 7,407,668 B2 Page 1 of 1
APPLICATION NO. : 10/057596
DATED : August 5, 2008
INVENTOR(S) : Douglas C. Shepard It is certified that error appears in the above-identified patent and that said Letters Patent is hereby corrected as shown below:

Specification, Col. 1, line 8, after "invention", delete "is".

Specification, Col. 1, line 30, before "because", delete ",".

Specification, Col. 3, line 63, before "of", change "portions" to -- portion --.

Specification, Col. 4, line 46, after "—NH—", change "(CH$_2$)n" to -- (CH$_2$)$_n$ --.

Specification, Col. 4, line 48, before "from 6 to 13", insert -- the range --.

Specification, Col. 4, line 49, before "6 to 12", change "form" to -- from --.

Claim 6, Col. 7, line 26, before "active", change "enzyrnatically" to -- enzymatically --.

Claim 8, Col. 7, line 30, before "active", change "enzyrnatically" to -- enzymatically --.

Claim 18, Col. 8, line 1, before "active", change "eazyinatically" to -- enzymatically --.

Signed and Sealed this

Twenty-first Day of April, 2009

JOHN DOLL
*Acting Director of the United States Patent and Trademark Office*